United States Patent [19]

Mantynen

[11] Patent Number: 6,107,349

[45] Date of Patent: *Aug. 22, 2000

[54] METHOD AND COMPOSITION FOR TREATING PSORIASIS

[76] Inventor: Philip R. Mantynen, 2515 Departure Bay Rd., Nanaimo, British Columbia, Canada, V9S 3W2

[ * ] Notice: This patent issued on a continued prosecution application filed under 37 CFR 1.53(d), and is subject to the twenty year patent term provisions of 35 U.S.C. 154(a)(2).

[21] Appl. No.: 09/062,786

[22] Filed: Apr. 16, 1998

[51] Int. Cl.$^7$ .................................................. C07D 311/72
[52] U.S. Cl. .............................. 514/863; 549/408; 426/72
[58] Field of Search ........................... 514/863; 549/408; 426/72

[56] References Cited

U.S. PATENT DOCUMENTS

| | | | |
|---|---|---|---|
| 5,221,533 | 6/1993 | Perlman | 424/73 |
| 5,290,809 | 3/1994 | Ippolito et al. | 514/458 |
| 5,444,092 | 8/1995 | Collins | 516/560 |
| 5,589,508 | 12/1996 | Schlotzer et al. | 514/560 |
| 5,607,921 | 3/1997 | Bernard et al. | |
| 5,633,284 | 5/1997 | Meyer. | |

*Primary Examiner*—Joseph McKane
*Assistant Examiner*—Taofiq A. Solola
*Attorney, Agent, or Firm*—Klarquist Sparkman Campbell Leigh & Whinston, LLP

[57] ABSTRACT

This invention pertains to the novel combination of Vitamin E, evening primrose oil and B-complex vitamins as a treatment for patients afflicted with psoriasis. It is postulated that the above compounds act synergistically to provide the cofactors required for normal skin production and repair in psoriatic patients.

11 Claims, No Drawings

METHOD AND COMPOSITION FOR TREATING PSORIASIS

FIELD OF THE INVENTION

This invention pertains to the use of a novel composition comprising Vitamin E, evening primrose oil and B-complex vitamins for treatment of patients afflicted with psoriasis. It is postulated that the above compounds act synergistically to provide the cofactors required for normal skin production in psoriatic patients.

BACKGROUND OF THE INVENTION

The skin is the largest organ in the human body and is in a state of constant turnover. This is accomplished by the outward movement of the basal layer keratinocytes at a rate that varies with age, sex, position on the body and other conditions. Psoriasis, an affliction of the epidermis, is a common disorder present in approximately 6.4 million people in the United States according to the National Psoriasis Foundation. The frequency of the disease varies with race, age, skin location and other conditions. The characteristic feature of psoriasis is hyperproliferation of the keratinocytes, first described by Van Scott and Ekel.[1] There is evidence of significant shortening of the epidermal cell cycle (36 hours versus 311 hours for normal tissue) in the involved skin of patients with psoriasis. In addition there is a doubling of the proliferative cell population and it appears that in psoriatic skin 100% of the germinative cells of the epidermis enter the growth fraction, compared to 60 to 70% for normal skin of non-psoriatic patients. It is felt that as a result of these changes there is an increase in size and in cohesiveness of corneocytes.[2] Transplantation studies of normal and psoriatic human skin to congenitally athymic nude mice have found that, although epidermal proliferation remains above normal in the transplanted psoriatic skin, the absence of clinical lesions (erythema, induration and scaling) suggests that epidermal proliferation does not itself give rise to psoriasis.

The fundamental cellular and metabolic defects underlying psoriasis are not well understood. Endothelial cells, mast cells and fibroblasts have been implicated in the pathogenesis of the disease.[3] Granulocytes are present in the spongioform microabscesses that constitute a hallmark of psoriasis and activation of isolated peripheral granulocytes correlates with disease severity.

Dermal fibroblasts are potent producers of cytokines and lipid mediators that may influence epidermal proliferation as well as the inflammatory reaction seen in psoriasis. Studies of the activity of membrane messenger systems have demonstrated that such systems are activated in psoriatic fibroblasts taken from lesional skin. In these studies the activity of membrane bound but not cytosolic phospholipid/Ca dependent protein kinase C (PKC) was significantly elevated.[4]

Peptide mediators are involved in the inflammatory cascade which takes place in the psoriatic skin. Complement split products, cytokines, interleukins and transforming growth factor alpha are found to be elevated in psoriatic skin.[5] They form part of the body's (defective) skin repair mechanism.

The cyclic nucleotides are not thought to be part of the basic molecular aberration in psoriasis, although it is now agreed that two basic alterations in the second messenger systems occur in psoriatic skin: (1) cyclic GMP levels are elevated in psoriatic lesions, and (2) stimulation of epidermal cells with a beta agonist leads to lower levels of cyclic AMP in the epidermis of lesional skin than in normal or uninvolved skin.[6]

The protease/antiprotease system has also come under scrutiny as increased protease activity has been noted in lesional skin. Proteases have the ability to regulate cell proliferation in other cell systems and can generate inflammatory mediators via the complement cascade.[7]

Utilization of fatty acids by keratinocytes appears to be fundamental to the development of psoriasis and is of relevance to the present invention. In particular, arachidonic acid and linoleic acid are polyunsaturated fatty acids which appear to be destined for different purposes in keratinocytes. Arachidonic acid is metabolized via the cyclooxygenase pathway predominantly into prostaglandins, such as PGE2, PGF2 Alpha, and PGD2, which modulate normal skin physiological processes at low concentrations and inflammatory reactions at high concentrations. Arachidonic acid is also metabolized via the lipoxygenase pathway into 15-hydroxyeicosatetraenoic acid (15-HETE) and other leukotrienes which function as potent inflammatory mediators. These mediators appear to play a role in producing the abnormalities typical of psoriatic lesions, such as infiltration of epidermal cells and epidermal hyperplasia as well as erythema and induration.[8]

The lipoxygenase pathway metabolizes linoleic acid into 13-hydroxy-9, 11-octadecadienoic acid (13-HODE). 13-HODE exerts anti-proliferative properties in keratinocytes, possibly via selective suppression of protein kinase C-beta isozyme activity.[9]

It appears that modulation of the cyclooxygenase and lipoxygenase metabolic pathways may influence psoriasis symptoms. For example, in some patients administration of nonsteroidal antiinflammatory medications (NSAIDS), which are known to inhibit the cyclooxygenase pathway, is associated with the onset or worsening of psoriasis symptoms. It may be that NSAIDS increase the amount of arachidonic acid substrate available to shunt down the lipoxygenase pathway, resulting in increased leukotriene production. By contrast, benoxaprofen, a drug that somewhat selectively blocks the lipoxygenase pathway, has been demonstrated to improve psoriatic symptoms in about 75% of patients studied.

Other findings suggest a possible link between fatty acid metabolism in skin cells and development of psoriasis. Dietary deficiencies of the essential fatty acids linoleic acid and gamma-linoleic acid are associated with increased levels of arachidonic acid and decreased PGE2. Moreover, deficiency of linoleic acid and gamma-linoleic acid has been shown to result in increased DNA synthesis and formation of a scaly dermatosis in some individuals. Also of interest is the finding that human skin fibroblasts preferentially increase linoleic acid incorporation into lipids (80% into phospholipids) and decrease arachidonic acid utilization as they age.[10] This may suggest an increased need for linoleic acid (and a heightened sensitivity to a deficiency thereof) as the fibroblasts age. This finding correlates with the clinical progression of psoriasis. Although psoriasis varies from patient to patient, the overall tendency is for the disease to gradually increase in severity as the patient ages.

Although the exact molecular disruption underlying psoriasis remains elusive, recent studies suggest that psoriasis is an immune-mediated disorder. Early and late onset psoriasis has been associated with certain HLA antigens which may help explain the inheritance pattern of the disease. Activated T cells are present in abnormally large quantities in active psoriatic skin. T cell derived cytokines are postulated to be candidates for inducing psoriatic changes as IL-2 therapy for malignancy in psoriatic patients has caused severe psoriatic exacerbation. Some therapies which suppress T cell development, such as administration of cyclosporin or psoralen plus Ultraviolet A (PUVA), have proven effective in clearing psoriasis lesions. While such therapies are effective in treating psoriasis, they also affect other cellular systems so the T cell changes may be but one of a number of factors in the pathogenesis of the disease.

Most current treatments for psoriasis act by regulating the immune system or otherwise attenuating the inflammatory response. Internal medications such as cyclosporin, methotrexate and retinoids all have potentially serious side effects such as liver and kidney damage, nausea, birth defects and increased cancer risk. Other common psoriasis treatments are also undesirable for long-term management of the disease. Extended use of topical corticosteroid creams may cause thinning of the skin, stretch marks and suppression of the patient's own cortisol production. Moreover, psoriatic symptoms tend to recur rapidly after cessation of corticosteroid use. Phototherapy can result in skin aging and increased risk of skin cancer.

The need has therefore arisen for a non-toxic, long-term treatment for psoriasis which does not merely attenuate inflammatory symptoms but endeavours to remedy local cellular nutritional deficiencies underlying the disease.

SUMMARY OF THE INVENTION

The invention relates to the use of a specific combination of Vitamin E, evening primrose oil and B-complex vitamins for treatment of psoriasis. It is postulated that the above compounds act synergistically to provide the cofactors required for normal skin production and repair in psoriatic patients. When administered alone, the compounds do not produce significant improvement in psoriasis, but when administered together orally they can significantly decrease the severity and extent of psoriasis present in afflicted patients. The compounds are non-toxic as compared to other oral medications available for the treatment of psoriasis, all which have significant adverse effects.

In accordance with the invention a method for treating psoriasis in a human patient is disclosed comprising administering to the patient on a continuing basis therapeutic amounts of Vitamin E, evening primrose oil and B-complex vitamins in combination. The B-complex vitamins preferably comprise folic acid and lipotropic factors, such as choline bitartrate and inositol. Preferably, the above compounds are administered daily by oral ingestion. The preferred daily dosages are within the following ranges:
Vitamin E: 400–1600 IU/day.
Evening primrose oil: 1–6 grams.
B-complex vitamins: 50–200 micrograms. (excluding folic acid)
Folic acid: 0.4–1.6 milligrams
More particularly, the method comprises administering to the patient on a daily basis therapeutic amounts in combination of (a) Vitamin E; (b) fatty acids selected from the group consisting of linoleic acid and gamma linoleic acid; and (c) B-complex vitamins selected from the group consisting of Vitamin B-1, Vitamin B-2, Vitamin B-3, Vitamin B-5, Vitamin B-6, Vitamin B-12, biotin, folic acid, para amino benzoic acid and lipotropic factors. Compositions for the treatment of psoriasis are also provided comprising combinations of the above compounds.

DETAILED DESCRIPTION OF THE PREFERRED EMBODIMENT

Definitions

As used herein the following terms shall have the following respective meanings:
"evening primrose oil" means oil extracted from evening primrose seeds and comprising linoleic acid and gamma-linoleic acid.
"Vitamin E" means d-alpha tocopherol.
"B-complex vitamins" means vitamins selected from the group consisting of Vitamin B-1 (thiamine hydrochloride), Vitamin B-2 (riboflavin), Vitamin B-3 (niacinamide), Vitamin B-5 (pantothenic acid or calcium pantothenate), Vitamin B-6 (pyridoxine hydrochloride), Vitamin B-12 (cyanocobalamine), biotin, folic acid, para amino benzoic acid and lipotropic factors.
"Lipotropic Factors" means factors which support lipid metabolism selected from the group consisting of choline bitartrate and inositol.
Description This invention relates to a method and composition for treating psoriasis comprising the use in combination of Vitamin E, evening primrose oil and B-complex vitamins. It is postulated that the above compounds act synergistically to provide the cofactors required for normal skin production in psoriasis patients.

Psoriatic skin turns over at an extremely rapid rate (approximately every four days as compared to twenty-eight days for normal skin). This results in a corresponding increase in demand for various metabolic substrates necessary for skin production. Although the precise metabolic defects underlying psoriasis remain unknown, the inventor has identified the essential fatty acid linoleic acid as one important metabolic substrate which may be deficient in psoriasis patients.

Keratinocytes utilize both linoleic acid and arachidonic acid. As discussed above, linoleic acid deficiencies may result in increased utilization of arachidonic acid in afflicted individuals via the lipoxygenase pathway, resulting in the production of inflammatory mediators such as leukotrienes which have been implicated in psoriasis pathogenesis. This effect is worsened by an increased amount of psoriasis and a corresponding increased rate of cell turnover. As the psoriatic lesions spread over a wider surface area of the patient's body, local cellular deficiencies of metabolic substrates such as linoleic acid will be exacerbated, resulting in a still greater likelihood that additional lesions will develop.

Apart from linoleic acid, various other metabolic substrates and cofactors undoubtedly play a role in skin cell production and repair in psoriasis patients. Vitamin E is postulated to have synergistic effect when added to linoleic acid and gamma-linoleic acid by inhibiting their peroxidation and by stabilizing the cell membrane.[11] Deficiencies in various of the B-complex vitamins have also associated with skin tissue disorders. Biotin, Vitamin B-1, and B-3 deficiencies produce scaling dermatoses. Vitamin B-5 is important in fatty acid synthesis. Vitamin B-6 is required for the desaturation and elongation of linoleic acid and may in such fashion influence prostaglandin production.

Folic acid, which is also a member of the B-complex family, is a necessary factor in skin replication. The drug methotrexate reduces hyperproliferation of the epidermis in psoriasis by inhibiting folic acid utilization. Serum folic acid deficiency is well documented in patients with longstanding psoriasis and may be in large measure contribute to their increased risk of vascular occlusive disease (due to increased homocysteine production).

The lipotropic factors choline bitartrate and inositol are necessary substrates for the formation of phospholipids that carry the monohydroxy fatty acids that may influence signal transduction and eicosanoid metabolism in psoriatic keratinocytes.

The inventor has postulated that the availability of fatty acids (such as linoleic acid and gamma-linoleic acid), Vitamin E, and various B-complex vitamins (including folic acid and lipotropic factors), may be insufficient in psoriasis patients due to rapid cell cycling. As set forth in the following case histories, it has been determined that oral supplementation of a combination of the above compounds results in a marked reduction in psoriasis symptoms, including psoriatic nail disease, in some afflicted individuals.

Case Histories

EXAMPLE 1

AB, a 50 year old female, had been suffering from chronic severe psoriasis for 31 years (since age 19). Over the years AB had tried various psoriasis treatments including topical and injected corticosteroids, coal tars, phototherapy, photochemotherapy (PUVA) and methotrexate. None of these treatments provided long-term relief from psoriasis symptoms. Following methotrexate treatment in 1990, AB was free from psoriasis symptoms for approximately six months. Symptoms then recurred and higher doses of methotrexate were prescribed which resulted in unacceptable side effects.

AB was administered the composition of the present invention for a trial period in the following daily dosages:
1. 800 I/U Vitamin E in a gelatin capsule
2. 1000 mg evening primrose oil in a gelatin capsule; and
3. B-complex vitamins, namely 100 mcg each of B-1, B-2, B-3, B-5, B-6, B-12, biotin, choline bitartrate; and 800 mcg folic acid.

At the commencement of treatment AB's psoriasis had flared and the symptoms were severe. Virtually AB's entire body was covered in psoriatic lesions except for her face. AB could not walk or bend her arms without severe discomfort. Within two weeks from the commencement of treatment AB noticed that the psoriatic lesions on her hands were healing. Within one month all of the psoriatic lesions on AB's upper body had cleared. At the end of a six week trial period AB was substantially free from psoriatic lesions, apart from some relatively small patches on her legs. The psoariatic lesions had largely been replaced with new skin tissue which was normal in appearance and pigmentation.

AB was then given a placebo drug combination in the following daily dosages:
1. 25,000 I/U Beta-carotene
2. 1000 mg Vitamin C
3. 2 capsules lactobacillus commensals (sold by Holista Health Foods under the trademark INTESTALIFE)

After approximately two weeks of placebo administration, AB's psoriasis symptoms began to recur. At the end of a six week trial period lesions had reappeared on her legs, hips and under her breasts.

EXAMPLE 2

CD, a 41 year old male, had been suffering from chronic, moderately severe psoriasis since age 12. Over the years CD had tried various psoriasis treatments including coal tars, topical steroidal creams, anthralin, calcipotriol and Ultraviolet B (UVB) light therapy. None of these treatments provided long-term relief from psoriasis symptoms. CD also had moderately severe psoriatic nail disease (onycholysis) which was unresponsive to treatment.

CD was administered oral supplements comprising the composition of the present invention for a trial period in the following typical daily dosages:
1. 800 I/U Vitamin E in a gelatin capsule
2. 2–3 g evening primrose oil in a gelatin capsule; and
3. B complex vitamins, namely 100 mcg each of B-1, B-2, B-3, B-5, B-6, B-12, biotin, choline bitartrate; and 800 mcg folic acid During the trial period CD experienced a 90% reduction in the severity of his psoriasis and his psoriatic nail disease symptoms cleared entirely. At one point during the trial period CD ceased taking the test composition for a period of two months. During this hiatus in treatment CD experienced a dramatic worsening of his psoriasis skin condition. When CD resumed the active drug treatment of the present invention following the two month hiatus, his skin condition once again improved markedly. The 90% reduction in the severity of psoriasis symptoms experienced by CD during the trial period has been maintained and tachyphylaxis has not occurred at the dosages set forth above.

EXAMPLE 3

EF, a 52 year old male, with a history of moderately severe psoriasis of 40 years duration was treated with oral supplements comprising the composition of the present invention. Previous treatments had no sustained benefit and included Goeckermann regimes (coal tar and UVB phototherapy), steroids and calcipotriol. The oral supplements of the present invention were administered for a trial period in the following daily dosages:
1. 800 I/U Vitamin E in a gelatin capsule
2. 3 g evening primrose oil in a gelatin capsule; and
3. B complex vitamins, namely 100 mcg each of B-1, B-3, B-5, B-6, B-12, biotin, choline bitartrate; and 800 mcg folic acid At the commencement of treatment date EF weighed approximately 100 kg and had approximately 25% skin surface area involvement with thick plaque psoriasis. During a two month trial period the plaque psoriasis lesions faded to flat pink patches. This clinical improvement has been sustained.

Summary

The use of evening primrose oil in combination with Vitamin E and B-complex vitamins (including folic acid and lipotropic factors choline bitartrate and inositol) has been shown to be a valuable adjunctive treatment in the management of psoriasis and indeed in some cases may obviate the need for other treatments to maintain normal appearing skin. The fact that these compounds may be administered orally as dietary supplements and are non-toxic in the appropriate prescribed doses makes this treatment approach especially appealing.

As should be apparent to someone skilled in the art, the preferred dosages of the active compounds of the invention are dependent on the size of the patient and the extent of skin surface area involvement. For example, very large patients with extensive psoriatic lesions have higher metabolic demands and consequently require higher dosages of the active compounds of the invention in order to achieve optimum results.

As will be apparent to those skilled in the art in the light of the foregoing disclosure, many alterations and modifications are possible in the practice of this invention without departing from the spirit of the scope thereof. Accordingly, the scope of the invention is to be construed in accordance with the combination of substances defined by the following claims.

REFERENCES

1. Van Scott E J, Ekel T M: Kinetics of Hyperplasia in Psoriasis. *Arch Dermatol* 88: 373, 1963.
2. Braun-Falco O et al: Abnormes Verhalten der epidermalen Regeneration bei Patienten mit Psoriasis Vulgaris. *Br J Dermatol* 229: 276, 1967.
3. Fitzpatrick T. B. et al. *Dermatology in General Medicine* p. 506, 1993.
4. Saiag P et al: Psoriatic induce hyperproliferation of normal keratinocytes in skin equivalent model in vitro. *Science* 230: 669, 1985.
5. Fitzpatrick T. B. et al: *Dermatology in General Medicine* p. 507, 1993.
6. Lowe N J et al: Cutaneous polyamines in psoriasis. *Br J Dermatol* 107: 21, 1982.
7. Fraki J E et al: Correlation of epidermal plasminogen activator activity with disease activity in psoriasis. *Br J Dermatol* 108: 39, 1983.
8. Voorhees J J: Leukotrienes and other lipoxygenase products in the pathogenesis and therapy of psoriasis. *Arch Dermatol* 119: 541, 1983.
9. Cho Y. Ziboh V A. *Biochemical & Biophysical Research Communications.* 201(1): 257–65, May 30, 1994.
10. Raederstorff D. Lochleiter V. Moser U. *International Journal for Vitamin & Nutrition Research.* 65(1): 51–5, 1995.
11. Nachbar F. Korting H C. The role of Vitamin E in Normal and damaged skin. *Journal of Molecular Medicine* 73(1) 7–17, January 1995.

What is claimed is:

1. A method for treating psoriasis in a human patient comprising administering to said patient by oral ingestion on a continuing basis therapeutic amounts in combination of Vitamin E, evening primrose oil, folic acid and B-complex vitamins selected from the group consisting of Vitamin B-1, Vitamin B-2 Vitamin 3, Vitamin B-6, Vitamin B-12, biotin, para amino benzoic acid and lipotropic factors.

2. The method of claim 1, wherein said therapeutic amounts are administered daily.

3. The method of claim 1, wherein the daily dosage of said Vitamin E is within the range of 400–1600 IU.

4. The method of claim 3, wherein the daily dosage of said evening primrose oil is within the range of 1–6 grams.

5. The method of claim 4, wherein the daily dosage of each of said B-complex vitamins is within the range of 50–200 micro grams.

6. The method of claim 5, wherein the daily dosage of said folic acid is within the range of 0.4–1.6 milligrams.

7. A method for treating psoriasis in a human being patient comprising administering to said patient on a daily basis therapeutic amounts in combination of (a) Vitamin E; (b) fatty acids selected from the group consisting of linoleic acid and gamma inoleic acid; (c) folic acid and (d) B-complex vitamins selected from the group consisting of consisting of Vitamin B-1, Vitamin B-2, Vitamin B-3, Vitamin B-5, Vitamin B-6, Vitamin B-12, biotin, para amino benzoic acid and lipotropic factors.

8. A composition for the treatment of psoriasis comprising in combination a pharmaceutical carrier suitable for oral administration and a therapeutically effective amount of:
    (a) Vitamin E;
    (b) evening primrose oil;
    (c) folic acid; and
    (d) B-complex vitamins selected from the group consisting of Vitamin B-1, Vitamin B-2, Vitamin B-3, Vitamin B-5, Vitamin B-6, Vitamin B-12, biotin, para amino benzoic acid and lipotropic factors.

9. A composition for the treatment of psoriasis comprising in combination a pharmaceutical carrier suitable for oral administration and a therapeutically effective amount of:
    (a) Vitamin E;
    (b) fatty acids selected from the group consisting of linoleic acid and gamma-linoleic acid;
    (c) folic acid; and
    (d) B complex vitamins selected from the group consisting of Vitamin B-1, Vitamin B-2, Vitamin B-3, Vitamin B-5, Vitamin B-6, Vitamin B-12, biotin, para amino benzoic acid and lipotropic factors.

10. A dietary supplement to be ingested orally for treatment of psoriasis comprising a pharmaceutical carrier suitable for oral administration and a therapeutically effective amount of:
    (a) Vitamin E;
    (b) evening primrose oil;
    (c) folic acid; and
    (d) B complex vitamins selected from the group consisting of Vitamin B-1, Vitamin B-2, Vitamin B-3, Vitamin B-5, Vitamin B-6, Vitamin B-12, biotin, para amino benzoic acid and lipotropic factors.

11. A method for treating psoriasis in a human patient comprising administering to said patient by oral ingestion on a continuing basis therapeutic amounts of Vitamin E; essential fatty acids selected from the group consisting of linoleic acid and gamma linoleic acid; folic acid; and B-complex vitamins selected from the group consisting of consisting of Vitamin B-1, Vitamin B-2, Vitamin B-3, B-5, Vitamin B-6, Vitamin b-12, biotin, para amino acid and lipotropic factors.

* * * * *